United States Patent
Matsuki et al.

(10) Patent No.: US 10,206,556 B2
(45) Date of Patent: Feb. 19, 2019

(54) MEDICAL POWER SUPPLY SYSTEM

(71) Applicant: OLYMPUS CORPORATION, Tokyo (JP)

(72) Inventors: Kaoru Matsuki, Kawasaki (JP); Akira Matsui, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 48 days.

(21) Appl. No.: 15/638,437

(22) Filed: Jun. 30, 2017

(65) Prior Publication Data
US 2017/0332881 A1 Nov. 23, 2017

Related U.S. Application Data

(63) Continuation of application No. PCT/JP2015/055833, filed on Feb. 27, 2015.

(51) Int. Cl.
*A61B 17/34* (2006.01)
*A61B 1/00* (2006.01)
(Continued)

(52) U.S. Cl.
CPC ...... *A61B 1/00029* (2013.01); *A61B 1/00124* (2013.01); *A61B 17/0218* (2013.01);
(Continued)

(58) Field of Classification Search
CPC . A61B 17/34; A61B 17/3401; A61B 17/3476; A61B 2017/00137; A61B 2017/00411; A61B 2017/00415
See application file for complete search history.

(56) References Cited

U.S. PATENT DOCUMENTS 4,535,773 A * 8/1985 Yoon ................. A61B 17/3496
600/566
4,804,054 A * 2/1989 Howson ............ A61B 17/3403
128/897
(Continued)

FOREIGN PATENT DOCUMENTS

JP H11-128242 A 5/1999
JP 2004-208922 A 7/2004
(Continued)

OTHER PUBLICATIONS

International Search Report dated May 12, 2015 issued in PCT/JP2015/055833.

*Primary Examiner* — Lynnsy Summitt
(74) *Attorney, Agent, or Firm* — Scully, Scott, Murphy & Presser, P.C.

(57) ABSTRACT

A medical power supply system includes: a medical device including an elongated insertion section, a power receiving unit including a power receiving member and movable relative to the insertion section in a longitudinal direction of the insertion section, and a biasing unit biasing the power receiving unit toward a distal end side of the insertion section; and a guide unit including a power transmitting unit including a power transmitting member, the insertion section being inserted into the guide unit. When the insertion section is inserted into the guide unit to a predetermined amount, the power receiving unit comes in contact with the power transmitting unit with being biased by the biasing unit, and the power transmitting member and the power receiving member face each other in an axial direction of the insertion section and have a positional relation in which wireless power transmission is possible.

9 Claims, 13 Drawing Sheets

(51) Int. Cl.
*A61B 18/12* (2006.01)
*A61B 17/02* (2006.01)
*H02J 50/10* (2016.01)
*A61B 17/29* (2006.01)
*A61B 18/14* (2006.01)
*A61B 17/00* (2006.01)

(52) U.S. Cl.
CPC .......... *A61B 17/34* (2013.01); *A61B 17/3403* (2013.01); *A61B 17/3476* (2013.01); *A61B 18/12* (2013.01); *A61B 1/00135* (2013.01); *A61B 17/29* (2013.01); *A61B 17/3478* (2013.01); *A61B 17/3498* (2013.01); *A61B 18/1442* (2013.01); *A61B 18/1482* (2013.01); *A61B 2017/00398* (2013.01); *A61B 2017/2925* (2013.01); *A61B 2017/3409* (2013.01); *H02J 50/10* (2016.02)

(56) References Cited

U.S. PATENT DOCUMENTS

| | | | | |
|---|---|---|---|---|
| 4,934,960 A * | 6/1990 | Capp | .................. | H01R 13/6625 333/185 |
| 5,344,420 A * | 9/1994 | Hilal | .................. | A61B 17/3417 606/16 |
| 5,380,321 A * | 1/1995 | Yoon | .................. | A61B 18/1402 606/41 |
| 5,417,687 A * | 5/1995 | Nardella | ............ | A61B 17/3476 604/164.08 |
| 5,472,447 A * | 12/1995 | Abrams | ......... | A61B 17/320068 604/22 |
| 5,599,347 A * | 2/1997 | Hart | .................. | A61B 17/3417 604/264 |
| 5,599,348 A * | 2/1997 | Gentelia | ............ | A61B 17/3462 604/164.01 |
| 5,733,323 A * | 3/1998 | Buck | ........................ | A61N 1/05 600/373 |
| 5,849,020 A * | 12/1998 | Long | .................. | A61B 18/1447 606/167 |
| 5,916,215 A * | 6/1999 | Long | .................. | A61B 18/1487 606/41 |
| 5,925,041 A * | 7/1999 | Long | ...................... | A61B 17/34 606/41 |
| 5,961,514 A * | 10/1999 | Long | ...................... | A61B 17/34 606/41 |
| 5,984,921 A * | 11/1999 | Long | ...................... | A61B 17/34 606/48 |
| 6,106,519 A * | 8/2000 | Long | .................. | A61B 18/1487 606/32 |
| 6,193,715 B1 * | 2/2001 | Wrublewski | ....... | A61B 18/1402 604/22 |
| 6,409,724 B1 * | 6/2002 | Penny | .................... | A61B 18/14 606/41 |
| 7,517,349 B2 * | 4/2009 | Truckai | .............. | A61B 18/1442 606/41 |
| 8,057,438 B2 * | 11/2011 | Bettuchi | ............ | A61B 17/3417 604/164.01 |
| 8,323,279 B2 * | 12/2012 | Dahla | ................ | A61B 18/1402 604/30 |
| 8,523,889 B2 * | 9/2013 | Stulen | ........... | A61B 17/320092 606/169 |
| 9,060,765 B2 * | 6/2015 | Rencher | ............... | A61B 18/042 |
| 9,297,866 B2 * | 3/2016 | Krueger | ................ | A61B 5/055 |
| 2004/0133189 A1 | 7/2004 | Sakurai | | |
| 2010/0179530 A1 * | 7/2010 | Long | .................. | A61B 18/1206 606/33 |
| 2014/0012247 A1 * | 1/2014 | Bakos | ................ | A61B 18/1477 606/33 |
| 2015/0057653 A1 * | 2/2015 | Sugiyama | .......... | A61B 17/3421 606/34 |
| 2015/0230858 A1 * | 8/2015 | Long | .................. | A61B 18/1477 606/41 |
| 2015/0333535 A1 * | 11/2015 | Feine | ..................... | A61C 17/20 307/104 |
| 2015/0359565 A1 * | 12/2015 | Matsui | ............... | A61B 17/3421 604/26 |
| 2015/0366434 A1 * | 12/2015 | Tsuruta | .............. | A61B 18/1442 600/104 |
| 2015/0366441 A1 * | 12/2015 | Tsuruta | .............. | A61B 1/00029 600/104 |
| 2015/0366610 A1 * | 12/2015 | Tsuruta | .............. | A61B 1/00029 606/46 |
| 2016/0183773 A1 * | 6/2016 | Sugiyama | .......... | A61B 17/3421 600/104 |
| 2016/0220101 A1 * | 8/2016 | Tsuruta | ................ | A61B 1/018 |
| 2017/0035402 A1 * | 2/2017 | Matsui | ................ | A61B 17/34 |
| 2017/0086906 A1 * | 3/2017 | Tsuruta | ................ | A61B 17/00 |
| 2017/0224412 A1 * | 8/2017 | Matsui | ............... | A61B 18/1482 |
| 2017/0245880 A1 * | 8/2017 | Honda | ........... | A61B 17/320068 |

FOREIGN PATENT DOCUMENTS

| | | |
|---|---|---|
| JP | 2008-206287 A | 9/2008 |
| JP | 4145395 B2 | 9/2008 |
| WO | WO 2015/025547 A1 | 2/2015 |

* cited by examiner

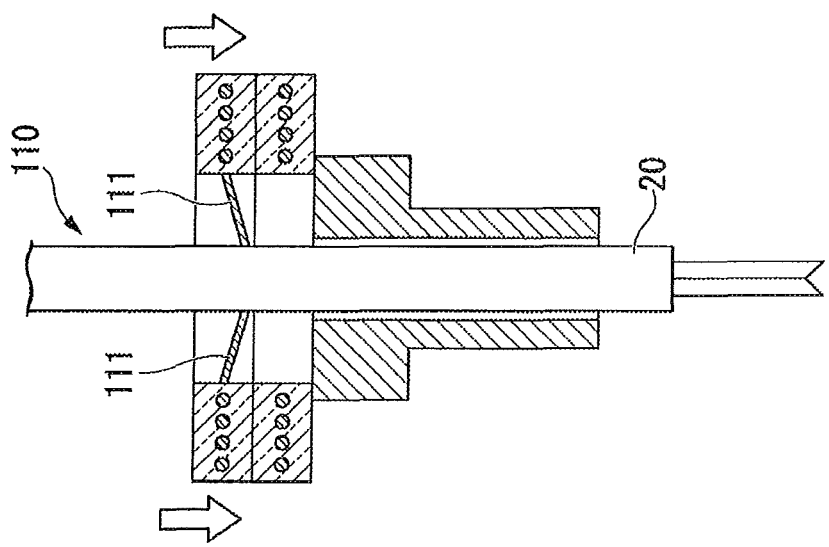
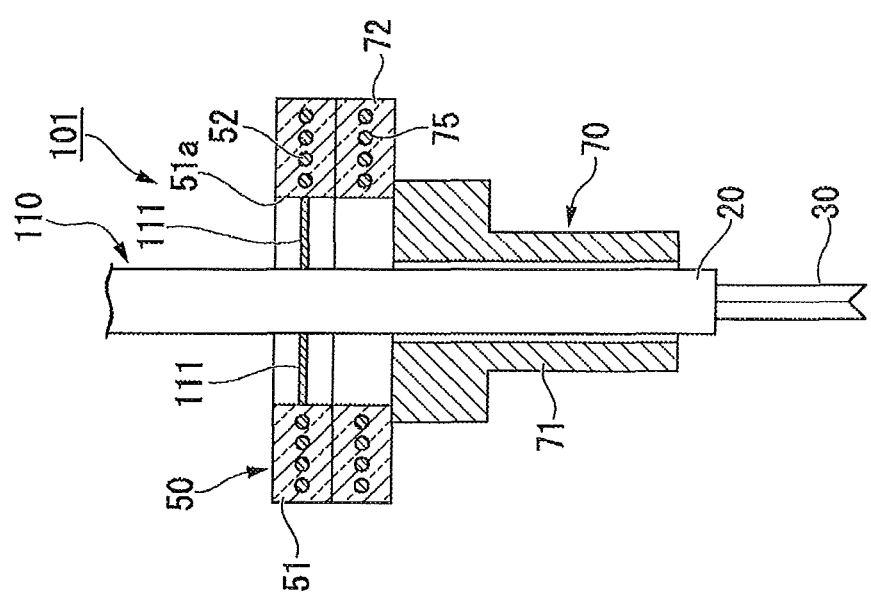
FIG. 7

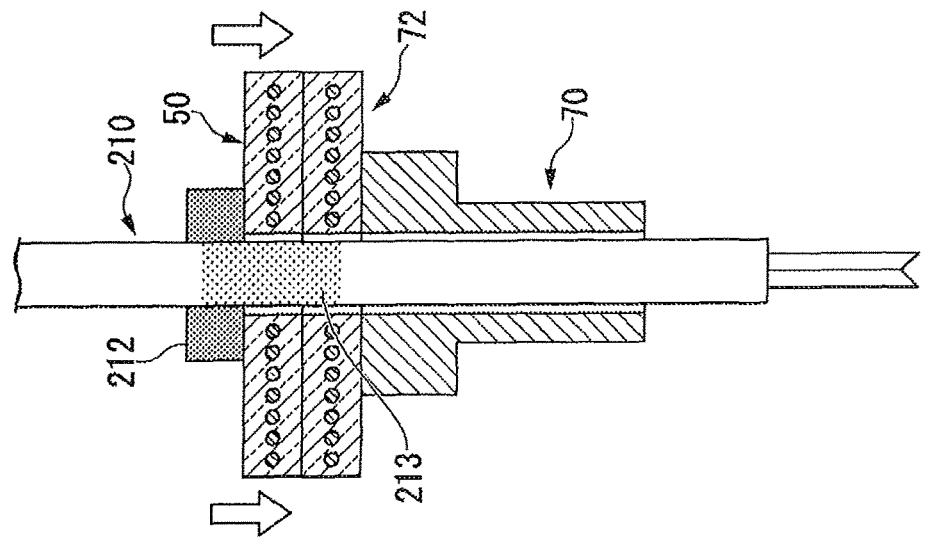
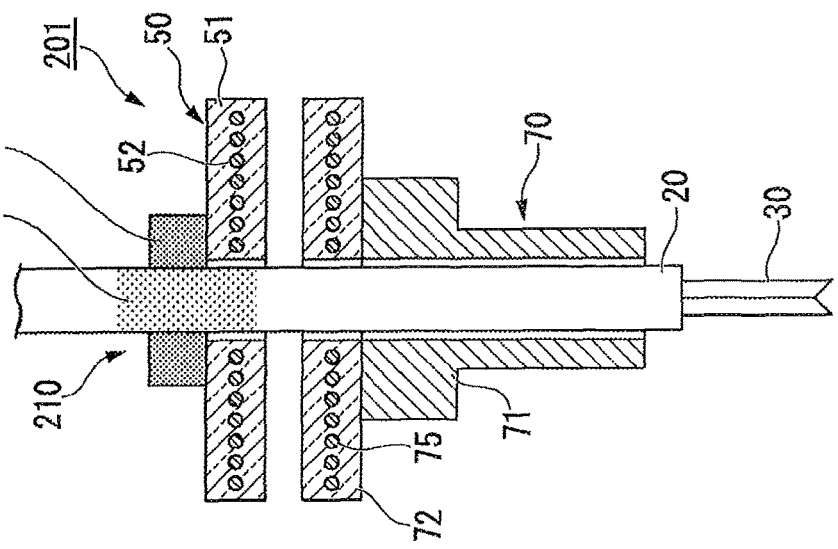
FIG. 8

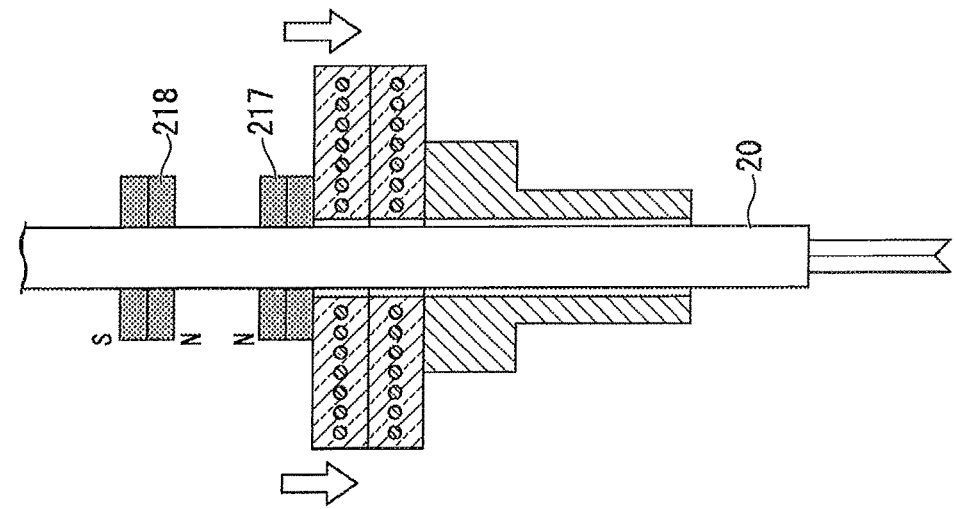
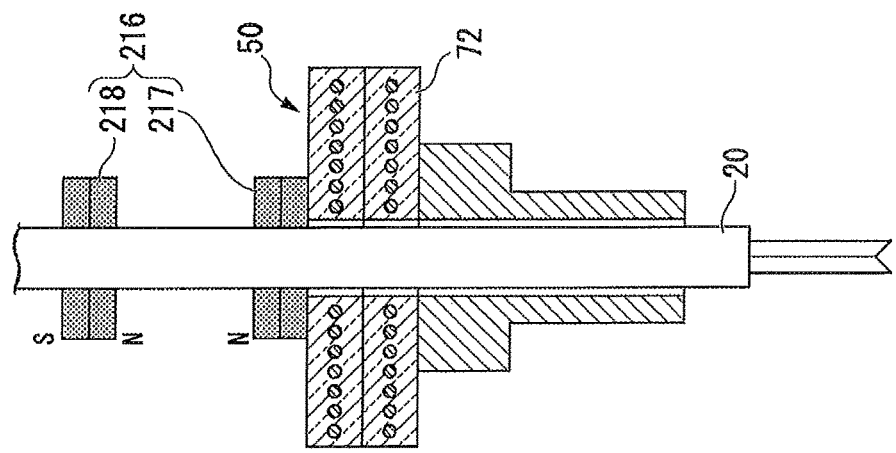

MEDICAL POWER SUPPLY SYSTEM

This application is a continuation application based on PCT Patent Application No. PCT/JP2015/055833, filed Feb. 27, 2015, the content of which is incorporated herein by reference.

BACKGROUND OF THE INVENTION

Field of the Invention

The present invention relates to a medical power supply system.

Description of Related Art

In the related art, various kinds of treatments using a trocar and a medical device while suppressing stress to a patient are known.

In a state in which the trocar is combined integrally with an inner needle having a sharp puncture section at a distal end thereof, the inner needle punctures a body wall of a patient so that the trocar is inserted into the abdominal cavity. After insertion into the abdominal cavity, the trocar is indwelled in the body wall by removing the inner needle, and used as a guide pipe for a treatment tool that performs treatment in the abdominal cavity.

The treatment tool serving as a medical device is inserted into the body of the patient via the trocar. When the treatment tool uses electric power to perform the treatment, the treatment tool is normally connected to a power supply source by a cable. The cable decreases manipulation performance when an operator performs the treatment.

In this regard, Japanese Patent No. 4145395 discloses a technology of preventing a decrease in manipulation performance of a treatment tool by performing wireless power transmission between a trocar and a medical device.

In the technology disclosed in Japanese Patent No. 4145395, as a primary coil disposed at a trocar and a secondary coil provided in a treatment tool inserted into the trocar are electromagnetically coupled, wireless power transmission from the trocar to the treatment tool can be performed. Accordingly, there is no need to connect the treatment tool to a power supply source via a cable.

SUMMARY OF THE INVENTION

According to a first aspect of the present invention, a medical power supply system includes: a medical device including an elongated insertion section, a distal end portion of which is provided with an end effector, a power receiving unit that includes a power receiving member and is movable relative to the insertion section in a longitudinal direction of the insertion section, and a biasing unit that biases the power receiving unit toward a distal end side of the insertion section; and a guide unit including a power transmitting unit at a proximal end side of the guide unit, the power transmitting unit including a power transmitting member connected to a power supply source, the insertion section of the medical device being inserted into the guide unit from the proximal end side of guide unit. When the insertion section is inserted into the guide unit to a predetermined amount, the power receiving unit comes in contact with the power transmitting unit in a state in which the power receiving unit is biased by the biasing unit, and the power transmitting member and the power receiving member face each other in an axial direction of the insertion section and have a positional relation in which wireless power transmission is possible.

According to a second aspect of the present invention, in the medical power supply system according to the first aspect, the power transmitting member and the power receiving member may be planar coils, and wireless power transmission may be performed through electromagnetic coupling of the power transmitting member and the power receiving member.

According to a third aspect of the present invention, in the medical power supply system according to the first or second aspect, the biasing unit may be a biasing member that is elastically deformable.

According to a fourth aspect of the present invention, in the medical power supply system according to the first or second aspect, the biasing unit may bias the power receiving unit using a magnetic force.

According to a fifth aspect of the present invention, the medical power supply system according to any one of the first to fourth aspects may further include: a first cover formed of a magnetic body and disposed to cover a portion of an outer surface of the power receiving unit; and a second cove formed of a magnetic body and disposed to cover a portion of an outer surface of the power transmitting unit. When the power receiving unit comes in contact with the power transmitting unit, the first cover and the second cover may cover surroundings of the power receiving member and the power transmitting member.

According to a sixth aspect of the present invention, in the medical power supply system according to the first aspect, the power transmitting member and the power receiving member may be planar electrodes, and wireless power transmission may be performed through electric field coupling of the power transmitting member and the power receiving member.

According to a seventh aspect of the present invention, the medical power supply system according to the sixth aspect may further include: a first cover formed of a conductive material and disposed to cover a portion of an outer surface of the power receiving unit; and a second cover formed of a conductive material and disposed to cover a portion of an outer surface of the power transmitting unit. When the power receiving unit comes in contact with the power transmitting unit, the first cover and the second cover may cover surroundings of the power receiving member and the power transmitting member.

According to an eighth aspect of the present invention, the medical power supply system according to the first aspect may further include a restriction unit that is provided at at least one of the power receiving unit and the power transmitting unit and restricts relative movement between the power receiving unit and the power transmitting unit in a radial direction of the insertion section in a state in which the power receiving unit comes in contact with the power transmitting unit.

According to a ninth aspect of the present invention, in the medical power supply system according to the first aspect, the power receiving unit may have a through-hole through which the insertion section is inserted.

BRIEF DESCRIPTION OF THE DRAWINGS

FIGS. 7(a) and 7(b) are partial cross-sectional views showing a process in use of a medical power supply system according to a second embodiment of the present invention.

FIGS. 8(a) and 8(b) are partial cross-sectional views showing a process in use of a medical power supply system according to a third embodiment of the present invention.

FIGS. 9(a) and 9(b) are partial cross-sectional view showing a process in use of a modified example of the medical power supply system.

DETAILED DESCRIPTION OF THE INVENTION

A first embodiment of the present invention will be described with reference to FIGS. 1 to 9. A medical power supply system of the embodiment includes a trocar (a guide unit) indwelled in a patient or the like, and a medical device inserted through the trocar and used.

Figure 1:
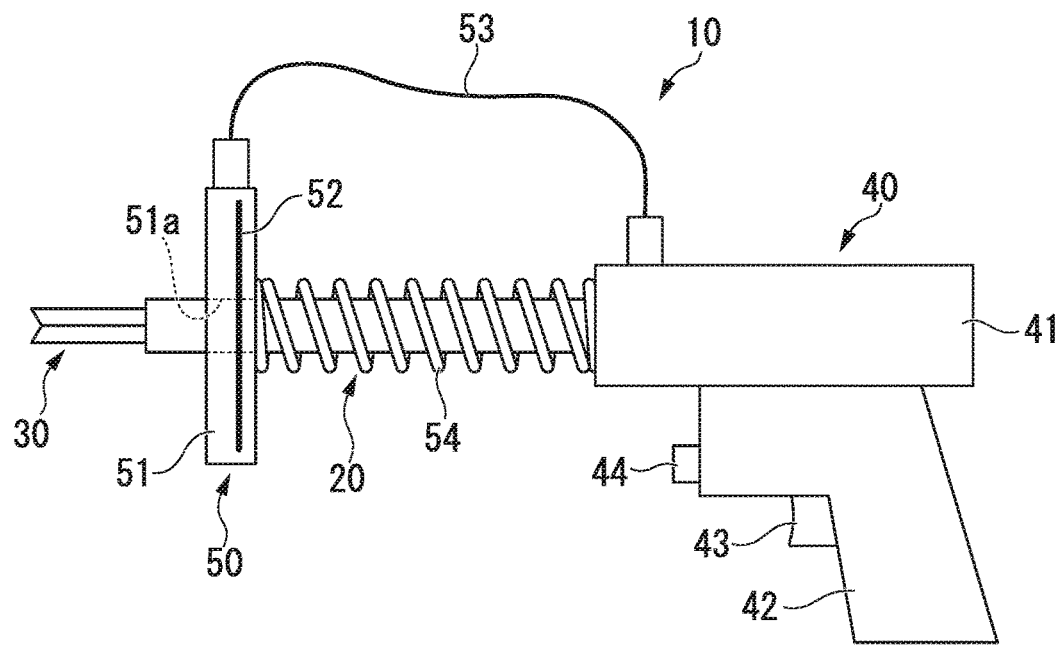
FIG. 1 is a side view showing a treatment tool serving as a medical device according to a medical power supply system of a first embodiment of the present invention.
Figure 2:
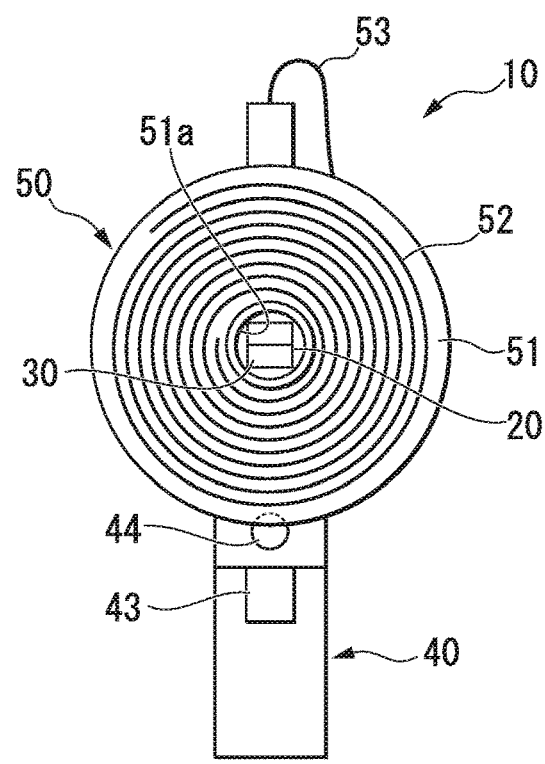
FIG. 2 is a front view of the treatment tool.

FIG. 1 is a side view showing a treatment tool 10 serving as the medical device. FIG. 2 is a front view of the treatment tool 10.

The treatment tool 10 includes an insertion section 20 that is at least partially inserted into the body of a patient or the like, a treatment unit (an end effector) 30 provided at a distal end portion of the insertion section 20, a manipulation unit 40 provided at a proximal end side of the insertion section 20, and a power receiving unit 50 attached to the insertion section 20 to be movable relative to the insertion section 20.

The insertion section 20 is formed of a metal, a resin, or the like in an elongated tubular shape. The treatment unit 30 of the embodiment is a forceps that can be opened and closed, and a basic structure thereof is known. When high-frequency current is supplied to the treatment unit 30 in a state in which tissue is grasped by the treatment unit 30, ablation, coagulation, hemostasis, or the like of the tissue can be performed. A driving member (not shown) for opening and closing the treatment unit 30 is formed of a conductor such as metal or the like in a rod shape or a wire shape. A distal end portion of the driving member is connected to the treatment unit 30. The driving member passes through the insertion section 20 to extend to the manipulation unit 40.

The manipulation unit 40 includes a main body 41 to which the insertion section is connected, a handle 42 grasped by a user, and a trigger 43 and a conduction button 44 that are manipulated by the user.

The driving member extending into the main body 41 is connected to the trigger 43, and when the user manipulates the trigger 43, the driving member is advanced and retracted to open and close the treatment unit 30.

The power receiving unit 50 includes a plate-shaped section 51 through which the insertion section 20 is inserted, and a planar coil (a power receiving member) 52 disposed at the plate-shaped section 51.

The plate-shaped section 51 is formed of an insulating material such as a resin or the like. As shown in FIGS. 1 and 2, a shape of the plate-shaped section 51 is a disk shape having a through-hole 51a at a center thereof. An inner diameter of the through-hole 51a is larger than an outer diameter of the insertion section 20, and the insertion section 20 can move relative to the power receiving unit 50 in a longitudinal direction of the insertion section 20 with no interference with the power receiving unit 50.

The planar coil 52 is formed by winding a metal strand on the same surface in a spiral shape. The planar coil 52 is disposed at an intermediate section in a thickness direction of the plate-shaped section 51 so as not to be exposed to an outer surface of the plate-shaped section 51. Since the plate-shaped section 51 of the embodiment is formed of a transparent resin, in FIGS. 1 and 2, the planar coil 52 is visible.

The power receiving unit 50 is electrically connected to the main body 41 by a cable 53. A first end portion of the cable 53 is electrically connected to the planar coil 52, and a second end portion thereof is electrically connected to the driving member in the main body 41 of the manipulation unit 40.

The power receiving unit 50 is connected to the manipulation unit 40 by a biasing member (a biasing unit) 54.

The biasing member 54 of the embodiment is a spiral spring. A first end portion of the biasing member 54 is connected to the plate-shaped section 51, and a second end portion thereof is connected to the main body 41.

According to the above-mentioned configuration, the power receiving unit 50 having the planar coil 52 is connected to the manipulation unit 40 by the cable 53 and the biasing member 54, and is movable relative to the insertion section 20 through deformation of the cable 53 and the biasing member 54. A length of the biasing member 54 is set such that the biasing member 54 is compressed in an axial direction when the treatment unit 30 of the treatment tool 10 inserted into the trocar protrudes from the trocar (which will be described below).

Figure 3:
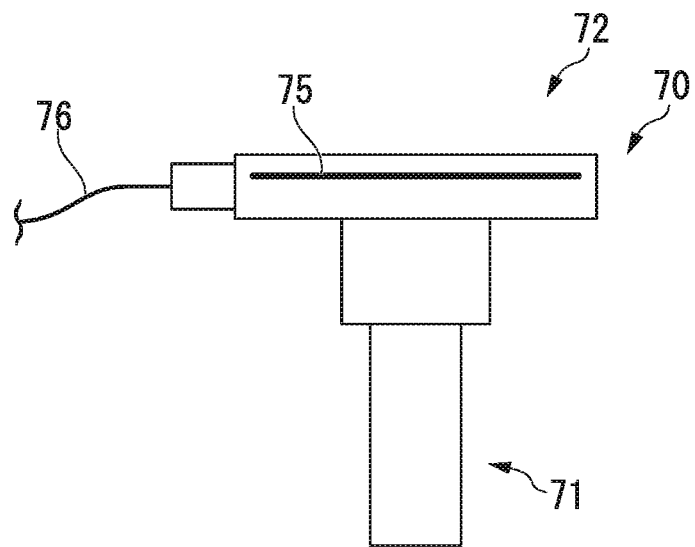
FIG. 3 is a side view showing a trocar serving as a guide unit according to the medical power supply system.
Figure 4:
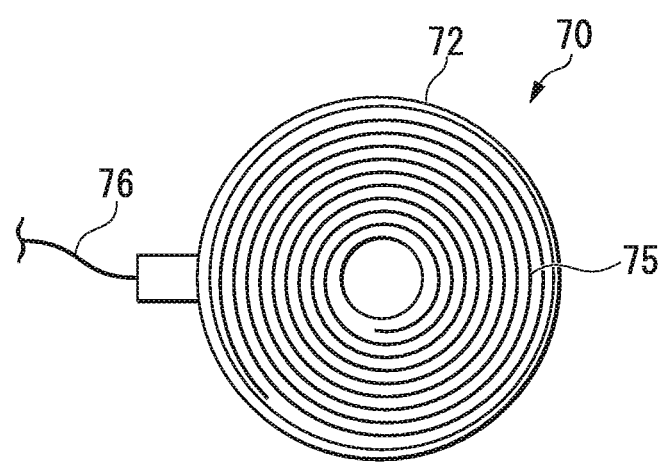
FIG. 4 is a plan view of the trocar.

FIG. 3 is a front view of a trocar 70. FIG. 4 is a plan view of the trocar 70. The trocar 70 includes a main body section 71 formed in a tubular shape, and a power transmitting unit 72 provided at the main body section 71.

A basic structure of the main body section 71 is similar to a known trocar, and the insertion section 20 of the treatment tool 10 can be inserted therethrough. The main body section 71 may have a valve for holding a pneumoperitoneum state, an inner needle for opening a hole in the abdominal wall, or the like according to necessity.

The power transmitting unit 72 has a planar coil (a power transmitting member) 75 and a transmission cable 76 electrically connected to the planar coil 75, and is fixed to a proximal end side of the main body section 71. A material and a shape of the power transmitting unit 72 and a disposition state of the planar coil 75 are generally similar to those of the plate-shaped section 51 and the planar coil 52 of the power receiving unit 50. The transmission cable 76 is electrically connected to a power supply source (not shown).

The planar coil 75 is visible because the power transmitting unit 72 of the embodiment is also formed of a transparent material. However, the plate-shaped section or the power transmitting unit may be formed of a color insulating material because the power receiving member and the power transmitting member need not be visibly disposed.

An operation in use of the medical power supply system of the embodiment including the treatment tool 10 and the trocar 70 configured as above will be described.

First, a user incises the abdominal wall of a patient or the like to form an opening in communication with the abdominal cavity. The main body section 71 of the trocar 70 is inserted into the opening from a distal end side thereof, and the trocar 70 is indwelled in the abdominal wall. The transmission cable 76 is connected to the power supply source. Connection between the transmission cable 76 and the power supply source may be performed either before or after indwelling of the trocar 70.

Figure 5:
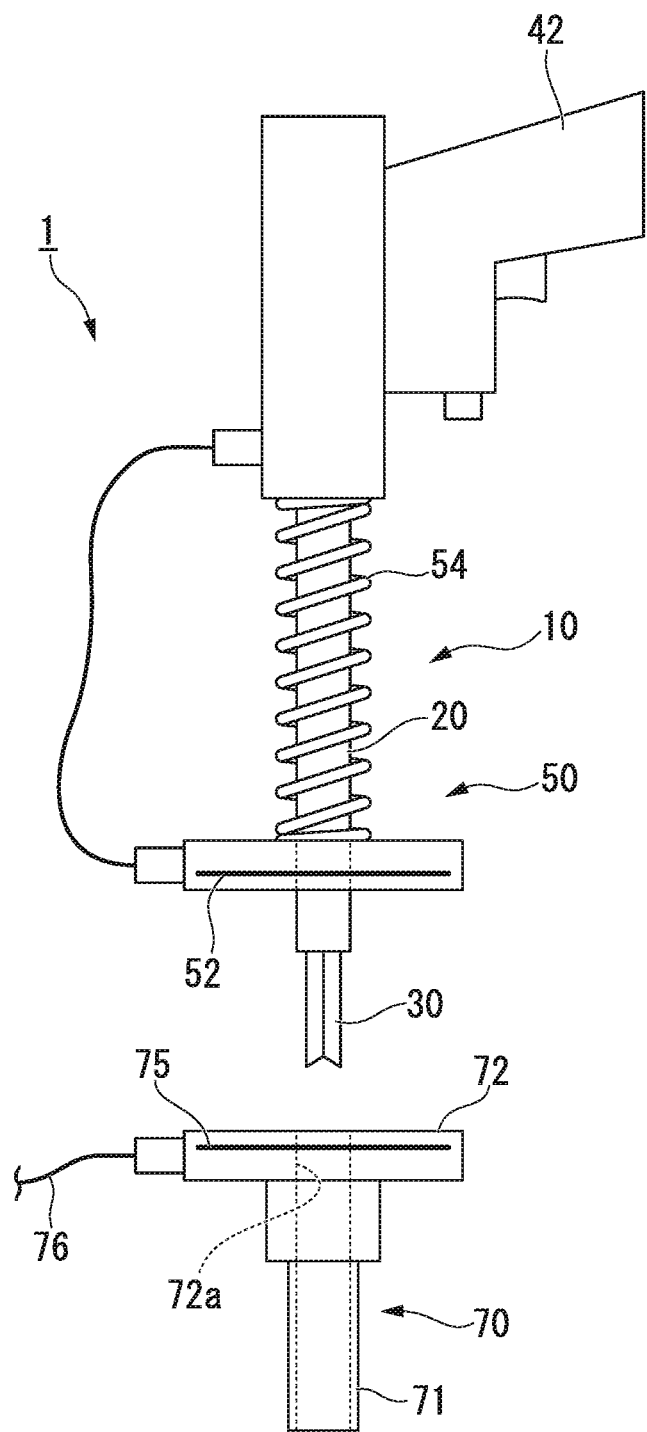
FIG. 5 is a view showing a process in use of the medical power supply system.
Figure 6:
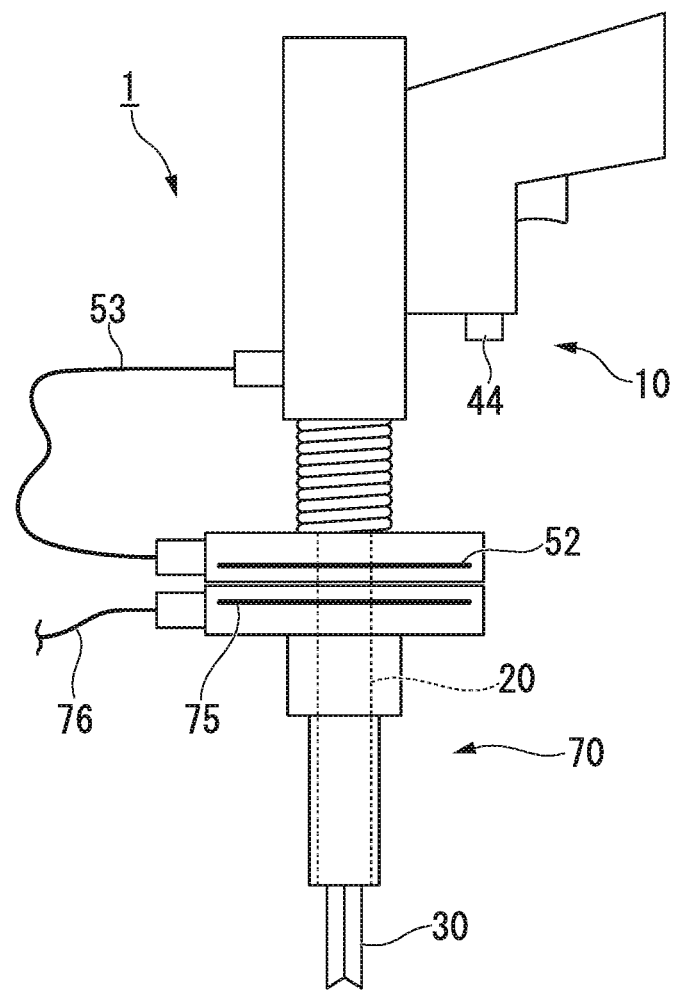
FIG. 6 is a view showing a process in use of the medical power supply system.

FIGS. 5 and 6 are views showing a process in use of the medical power supply system 1. As shown in FIG. 5, the user grasps the handle 42 of the treatment tool 10 and inserts the treatment unit 30 into the trocar 70 from a proximal end side of the trocar 70. First, the treatment unit 30 enters the main body section 71 through a through-hole 72a of the power transmitting unit 72, and then the insertion section 20 enters the main body section 71.

When the treatment tool 10 is inserted into the trocar 70 to some extent, the power transmitting unit 72 of the trocar 70 comes in contact with the power receiving unit 50. Accordingly, the planar coil 75 disposed at the power transmitting unit 72 and the planar coil 52 disposed at the power receiving unit 50 face each other in the longitudinal direction of the insertion section 20 outside in a radial direction of the insertion section 20. When the treatment tool 10 is further inserted, the treatment unit 30 and the insertion section 20 are moved relative to the trocar 70 toward the distal end side of the main body section 71. Here, by compressing the biasing member 54, the power receiving unit 50 holds a contact state with the power transmitting unit 72 and does not move relative to the trocar 70. In addition, the power receiving unit 50 is biased toward the power transmitting unit 72 and suppressed from being separated from the power transmitting unit 72 by a force of the compressed biasing member 54 returning to its original shape.

Before long, as shown in FIG. 6, the treatment unit 30 of the treatment tool 10 protrudes from the trocar 70. In this state, the user can perform various kinds of treatments using the treatment tool 10.

When the user wants to energize the treatment unit 30, the user presses the conduction button 44 of the manipulation unit. Power supplied from the power supply source is transmitted from the transmission cable 76 to the planar coil 75. As the planar coil 75 and the planar coil 52 disposed to face each other in the longitudinal direction of the insertion section 20 are electromagnetically coupled, power is transmitted from the power transmitting unit 72 to the power receiving unit 50 through wireless power transmission. After that, power is supplied to the treatment unit 30 via the cable 53 and driving member.

While the treatment is performed, the treatment tool 10 is advanced or retracted in the longitudinal direction of the insertion section 20 or rotated around the axis of the insertion section 20 with respect to the trocar 70, or inclined with respect to the trocar 70. However, in a state in which the treatment unit 30 protrudes from the trocar 70, the biasing member 54 is constantly compressed and biases the power receiving unit 50 toward the power transmitting unit 72. Accordingly, during the treatment, regardless of a position, an orientation, or the like of the treatment tool 10, a facing state of the planar coil 75 and the planar coil 52 is appropriately held and hardly changed. As a result, stable wireless power transmission can be consistently performed during the treatment.

As described above, the medical power supply system 1 of the embodiment is configured to perform wireless power transmission by electromagnetically coupling the power transmitting unit 72 provided at the trocar 70 and the power receiving unit 50 provided at the treatment tool 10 outside in the radial direction of the insertion section 20 and outside the trocar 70. That is, in the medical power supply system 1, since a radial dimension of the insertion section of the medical device inserted into the trocar 70 does not exert an influence on transmission efficiency of wireless power transmission, even when the radial dimension of the insertion section differs at each of the used medical devices, properties of the wireless power transmission can be the same in all medical devices. Accordingly, flexibility in design of medical devices can be remarkably improved, and the properties of the wireless power transmission can be unified in all medical devices.

In addition, since an area of the electromagnetically coupled portion can be increased with no variation in dimension of the insertion section, reduction in size of the portion of the medical device inserted into the body and improvement of transmission efficiency can be easily compatible.

Further, since the biasing member 54 that biases the power receiving unit 50 toward the distal end side of the insertion section 20 is provided, a state in which the power transmitting unit 72 and the power receiving unit 50 come in appropriate contact with each other is held during the treatment using the treatment tool 10. Accordingly, appropriate wireless power transmission can be consistently performed regardless of a position or an orientation of the treatment tool 10, an indwelling angle of the trocar 70, or the like.

Next, a second embodiment of the present invention will be described with reference to FIGS. 7(a) and 7(b). A medical power supply system 101 of the embodiment is distinguished from the above-mentioned medical power supply system 1 in the configuration of the biasing unit. In the following description, the same components as described above are designated by the same reference numerals and overlapping description will be omitted.

FIGS. 7(a) and 7(b) are partial cross-sectional views showing a process in use of the medical power supply system 101. The medical power supply system 101 includes a treatment tool 110 serving as a medical device, and the trocar 70. The treatment tool 110 is distinguished from the treatment tool 10 of the first embodiment only in that a leaf spring 111 serving as a biasing unit is provided instead of the biasing member 54.

Two leaf springs 111 are attached to an inner surface of the through-hole 51a of the plate-shaped section 51, and the plate-shaped section 51 is connected to an outer surface of the insertion section 20 by the leaf springs 111. The leaf springs 111 have a shape in which a surface direction is substantially parallel to the plate-shaped section 51 in a natural state in which no force is applied. The number or disposition of the leaf springs 111 can be appropriately set.

In the medical power supply system 101 having the above-mentioned configuration, like the first embodiment, when the treatment tool 110 is inserted into the trocar 70, as shown in FIG. 7(a), first, the power receiving unit 50 and the power transmitting unit 72 come in contact with each other, and wireless power transmission becomes possible. Further, when the treatment tool 110 is pushed into the trocar 70 to advance, since only the insertion section 20 advances while the position of the power receiving unit 50 does not vary, as shown in FIG. 7(b), the leaf springs 111 are pulled toward the trocar 70. As the leaf springs 111 elastically deformed by the pulling return to its original shape, a biasing force of biasing the power receiving unit 50 toward the power transmitting unit 72 occurs as shown by an arrow in FIG. 7(b).

According to the medical power supply system 101 of the embodiment, like the first embodiment, reduction in size of the medical device and improvement of transmission efficiency of wireless power transmission can be easily compatible, and appropriate wireless power transmission can be consistently performed.

Since a stroke of elastic deformation of the leaf spring 111 is frequently smaller than a stroke of elastic deformation of the biasing member 54, in the embodiment, the power receiving unit 50 is preferably attached to a position closer to the manipulation unit 40 than that in the first embodiment.

Next, a third embodiment of the present invention will be described with reference to FIGS. 8(a) to 9(b). A medical power supply system 201 of the embodiment is distinguished from the medical power supply systems of the above-mentioned embodiments in the configuration of the biasing unit.

FIGS. 8(a) and 8(b) are partial cross-sectional views showing a process in use of the medical power supply system 201. The medical power supply system 201 includes a treatment tool 210 serving as a medical device, and the trocar 70. A biasing unit 211 of the treatment tool 210 includes a permanent magnet 212 attached to a proximal end side of the plate-shaped section 51, and a magnetic body section 213 provided at an outer surface of the insertion section 20. In the embodiment, the power receiving unit 50 is connected to the manipulation unit 40 by the cable 53 (not shown) only. The magnetic body section 213 is provided only within a certain range in the axial direction of the outer surface of the insertion section 20. The magnetic body section 213 may be formed by, for example, disposing a magnetic body on the outer surface of the insertion section 20 through coating or the like (for example, nickel coating or the like).

An operation in use of the medical power supply system 201 configured as above will be described.

Before the treatment tool 210 is inserted into the trocar 70, the power receiving unit 50 is held at a predetermined position by the permanent magnet 212 and the magnetic body section 213 attracting each other. As shown in FIG. 8(a), when the treatment tool 210 is inserted into the trocar 70, the power receiving unit 50 and the power transmitting unit 72 come in contact with each other, and wireless power transmission becomes possible. Further, when the treatment tool 210 is pushed into the trocar 70 to advance, as shown in FIG. 8(b), only the insertion section 20 advances without variation in the position of the power receiving unit 50, and the magnetic body section 213 advances with respect to the permanent magnet 212. As a result, a biasing force of biasing the power receiving unit 50 toward the power transmitting unit 72 occurs as shown by an arrow of FIG. 8(b) due to a magnetic force working between the permanent magnet 212 and the magnetic body section 213.

In the medical power supply system 201 of the embodiment, like the above-mentioned embodiments, reduction in size of the medical device and improvement of transmission efficiency of wireless power transmission can be easily compatible, and appropriate wireless power transmission can be consistently performed.

While an example of the biasing unit using an attractive force generated by a magnetic force as a biasing force has been described above, instead of this, a biasing unit may be configured to use a repulsive force generated by a magnetic force as a biasing force.

In a modified example shown in FIGS. 9(a) and 9(b), a biasing unit 216 is constituted by a first magnet 217 attached to the power receiving unit 50 and a second magnet 218 fixed to the insertion section 20. The first magnet 217 and the second magnet 218 are disposed such that N-poles face each other.

In the case of the modified example, when the insertion section 20 is advanced after the power receiving unit 50 and the power transmitting unit 72 come in contact with each other, the first magnet 217 and the second magnet 218 approach each other to generate a repulsive force therebetween. The biasing force of biasing the power receiving unit 50 toward the power transmitting unit 72 is generated by the repulsive force as shown by an arrow of FIG. 9(b). In the above-mentioned configuration, appropriate wireless power transmission can be consistently performed regardless of a position or orientation of the treatment tool, an indwelling angle of the trocar, or the like.

Next, a fourth embodiment of the present invention will be described with reference to FIGS. 10 to 13. A medical power supply system 301 of the embodiment is distinguished from the medical power supply systems of the above-mentioned embodiments in that the power transmitting unit and the power receiving unit include covering members formed of magnetic bodies.

Figure 10:
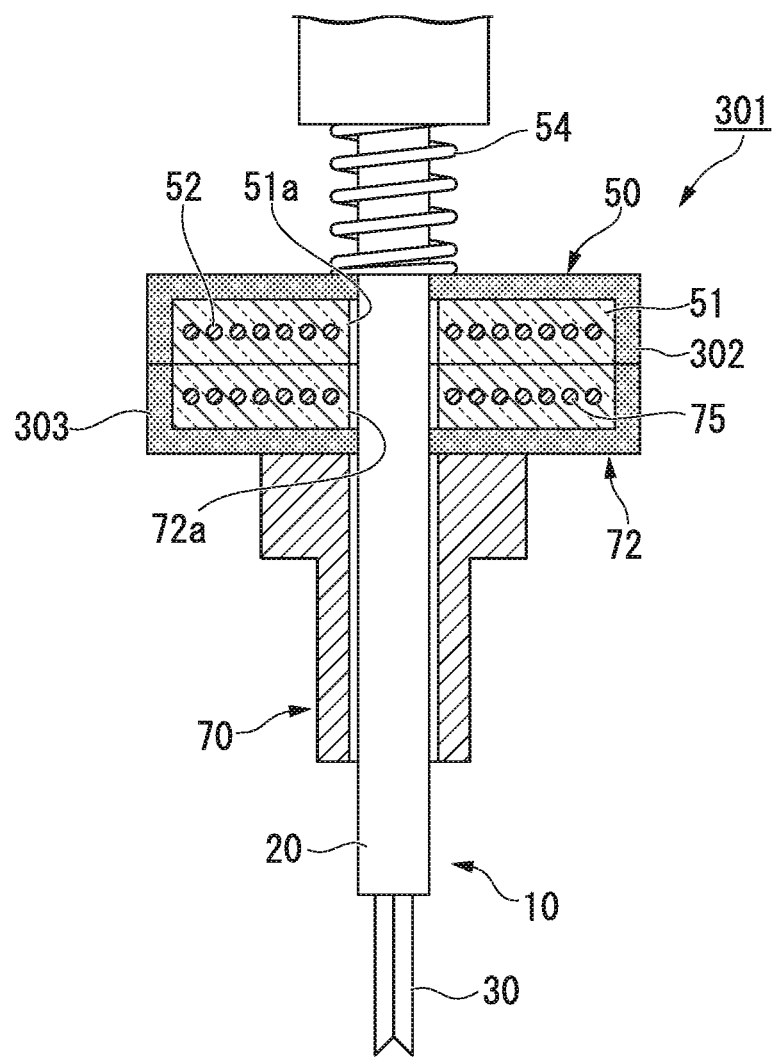
FIG. 10 is a partial cross-sectional view showing a process in use of a medical power supply system according to a fourth embodiment of the present invention.
Figure 11:
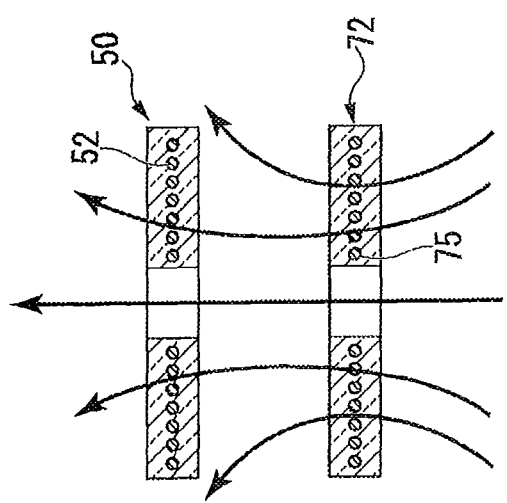
FIG. 11(a) is a view schematically showing a magnetic field in a state in which no covering member is provided.
FIG. 11(b) is a view schematically showing a magnetic field in a state in which a covering member is provided.
Figure 11:
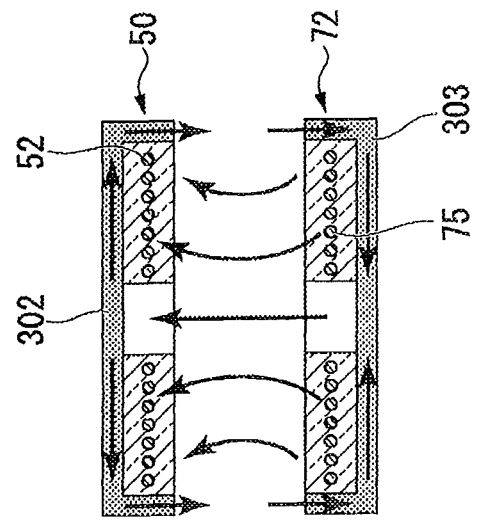

FIG. 10 is a cross-sectional view showing a process in use of the medical power supply system 301. FIG. 10 shows a state in which the power receiving unit 50 and the power transmitting unit 72 come in contact with each other and the power receiving unit 50 is biased by the biasing member 54. In the state in which the power receiving unit 50 and the power transmitting unit 72 come in contact with each other, outer surfaces of the power receiving unit 50 and the power transmitting unit 72 are covered by a first covering member (first cover) 302 provided at the power receiving unit 50 and a second covering member (second cover) 303 provided at the power transmitting unit 72.

The first covering member 302 is formed of a magnetic body and disposed to cover all surfaces of the outer surfaces of the power receiving unit 50 except for a surface facing the power transmitting unit 72, an inner surface of the through-hole 51a, and a portion at which the cable 53 (not shown) is disposed. The second covering member 303 is formed of a magnetic body and disposed to cover all surfaces of the outer surfaces of the power transmitting unit 72 except for a surface facing the power receiving unit 50, an inner surface of the through-hole 72a, and a portion at which the transmission cable 76 (not shown) is disposed. For example, a soft magnetic material such as Permalloy, silicon steel, or soft ferrite may be used as a magnetic body that forms the first covering member 302 and the second covering member 303.

In the medical power supply system 301 of the embodiment, like the above-mentioned embodiments, reduction in size of the medical device and improvement of transmission efficiency of wireless power transmission can be easily compatible, and appropriate wireless power transmission can be consistently performed.

In addition, when the power receiving unit 50 and the power transmitting unit 72 come in contact with each other and the planar coil 52 and the planar coil 75 face each other to be magnetic-field-coupled, the outsides of the two planar coils are covered by the first covering member 302 and the second covering member 303 formed of the magnetic body. Accordingly, as shown in FIG. 11(b), a leakage magnetic field generated from the planar coil 52 and the planar coil 75 is trapped by the magnetic body. As a result, in comparison with the state in which the outsides of the two planar coils are not covered as shown in FIG. 11(a), a closed circuit is formed at portions of the two planar coils, a larger amount of magnetic flux can be directed toward the planar coil 52, and transmission efficiency can be improved.

Further, since the outsides of the two planar coils are covered by the magnetic bodies, influence of the magnetic field on a human body or peripheral devices can be reduced. In FIGS. 11(a) and 11(b), a state of the magnetic field is shown by an arrow.

Since the covering configuration by the magnetic body described in the embodiment exhibits the above-mentioned effects, the covering configuration may also be applied to the medical power supply system that does not include the biasing unit.

A modified example of the embodiment will be described below.

Figure 12:
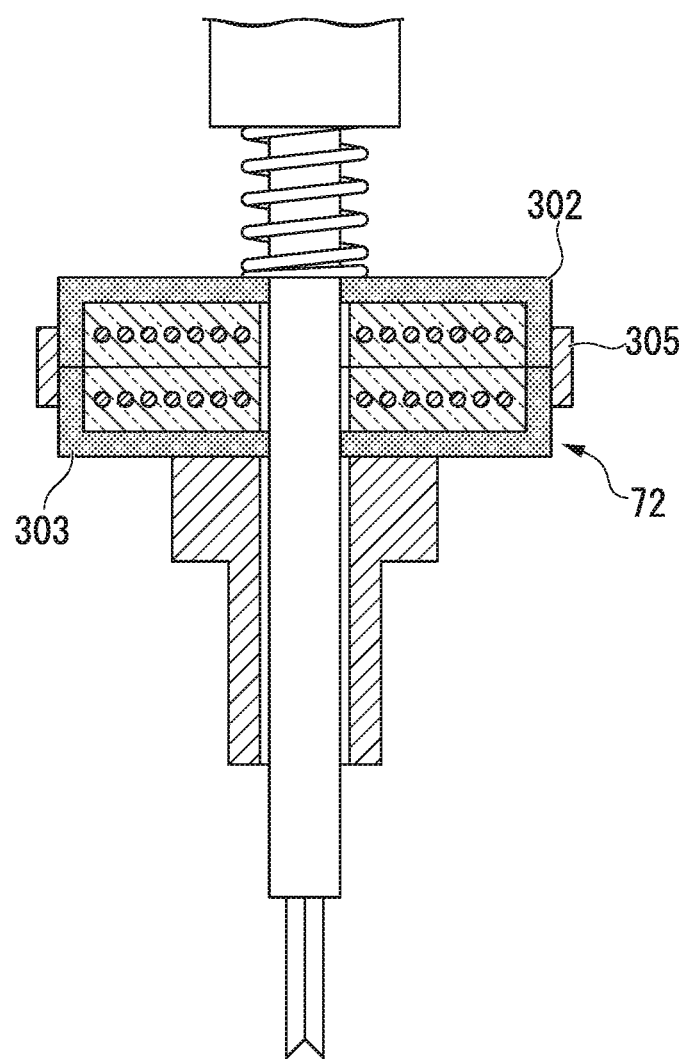
FIG. 12 is a partial cross-sectional view showing a process in use of a modified example of the medical power supply system.

In the modified example shown in FIG. 12, a ring-shaped restriction member (a restriction unit) 305 is attached to the first covering member 302. The restriction member 305 and the first covering member 302 are integrally joined to each other as an inner circumferential surface of the restriction member 305 is joined to an outer circumferential surface of the first covering member 302, and a portion of the restriction member protrudes toward the power transmitting unit 72.

When the power receiving unit 50 and the power transmitting unit 72 come in contact with each other, as shown in FIG. 12, since the power transmitting unit 72 enters an inside of the ring-shaped restriction member 305, the power receiving unit 50 and the power transmitting unit 72 are suppressed from moving relative to each other in the radial direction (the surface direction of the planar coil) after contact. As a result, stable power transmission can be performed.

In the modified example, the restriction member may be attached to the second covering member 303. In addition, the restriction member may not be formed in a ring shape but may be provided at a plurality of places (for example, three places) in the circumferential direction of the covering member at intervals.

Figure 13:
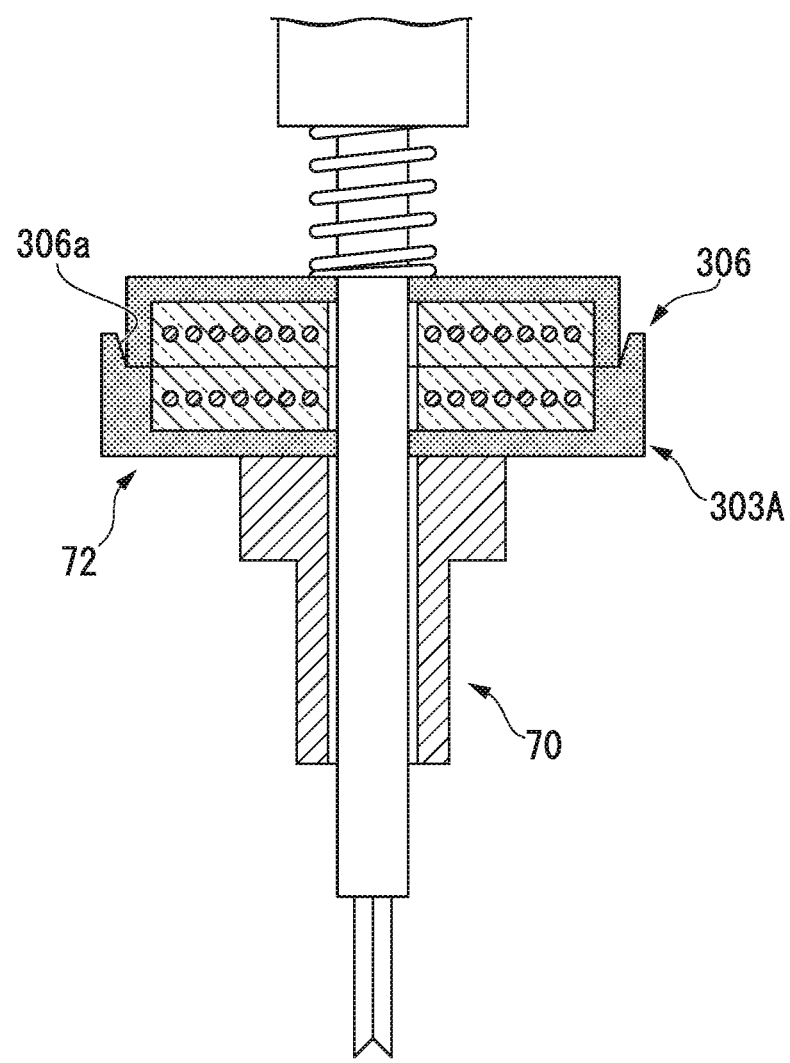
FIG. 13 is a partial cross-sectional view showing a process in use of a modified example of the medical power supply system.

The modified example shown in FIG. 13 is a configuration in which a second covering member 303A itself has a relative movement suppression function. The second covering member 303A has a circumferential edge portion protruding toward the power receiving unit 50 and serving as a guide unit 306. An inner circumferential surface 306a of the guide unit 306 is formed in a tapered shape in which an inner diameter is reduced toward the distal end side of the trocar 70.

In the modified example, the power receiving unit 50 and the power transmitting unit 72 can be suppressed from moving relative to each other in the radial direction after they come in contact with each other.

In addition, since the inner circumferential surface 306a of the guide unit 306 is formed in a tapered shape, even when the power receiving unit 50 deviates slightly in the radial direction when approaching the power transmitting unit 72, the power receiving unit 50 can be guided by the inner circumferential surface 306a to move smoothly to the inside of the guide unit 306 so that the power receiving unit 50 can come in contact with the power transmitting unit 72.

Further, since the restriction unit described in the modified examples may not be provided at the covering member, the restriction unit may be applied to all embodiments of the present invention. For example, even when the restriction member is directly attached to the power receiving unit or the power transmitting unit or a portion of the plate-shaped section or the power transmitting unit is formed to exhibit a function of the restriction member, the power receiving unit and the power transmitting unit can be suppressed from moving relative to each other in the radial direction after they come in contact with each other.

Although the embodiments of the present invention have been described above, the technical scope of the present invention is not limited to the above-mentioned embodiments. The components may be variously combined, modified, or deleted without departing from the scope of the present invention.

Figure 14:
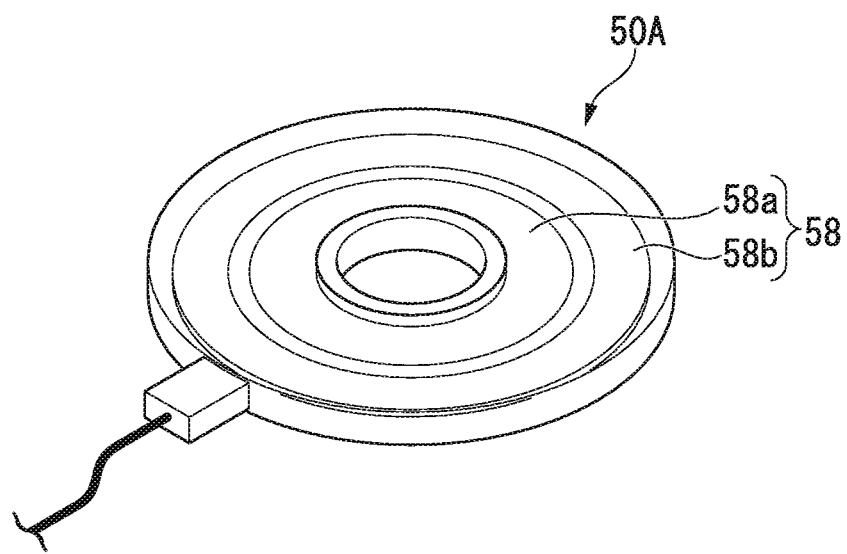
FIG. 14 is a perspective view showing another example of a power receiving unit of the medical power supply system of the present invention.
Figure 15:
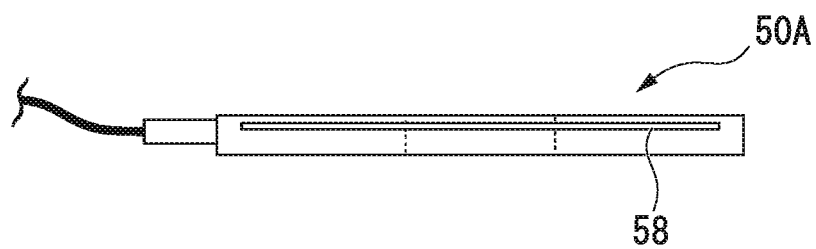
FIG. 15 is a side view of the power receiving unit.

While the example in which wireless power transmission is performed by electromagnetic coupling of the planar coils disposed at the power transmitting unit and the power receiving unit has been described in the above-mentioned embodiments, the configuration of the present invention is not limited thereto. For example, like a power receiving unit 50A of a modified example shown in FIGS. 14 and 15, wireless power transmission may be performed in a configuration in which a planar electrode 58 formed of a metal foil or the like is disposed instead of the planar coil and faces a planar electrode disposed at the power transmitting unit and having the same shape as the planar electrode 58 with an insulating material sandwiched therebetween. In this case, the planar electrodes facing each other between the power receiving unit and the power transmitting unit are connected by electric field coupling.

The planar electrode 58 of the power receiving unit 50A has two regions 58a and 58b, which are electrically divided. In the example, the two regions 58a and 58b are divided in a concentric circular shape to surround the through-hole of the power receiving unit, and areas of the two regions 58a and 58b are substantially the same. As described above, since a shape of the planar electrode of the power transmitting unit is also the same, as the power receiving unit and the power transmitting unit face each other, two pairs of planar electrodes facing each other between the power receiving unit and the power transmitting unit are formed, and wireless power transmission from the power transmitting unit to the power receiving unit can be performed by electric field coupling between the facing planar electrodes. As two regions of the planar electrode are divided in a concentric circular shape, even when the power receiving unit is moved (rotated) around an axis of the insertion section with respect to the power transmitting unit in accordance with manipulation of the medical device, stable power transmission becomes possible without variation in area of the facing electrodes. Further, the plurality of regions of the planar electrode may not be divided in a concentric circular shape as long as the power transmitting unit and the power receiving unit are configured to face each other consistently in a predetermined positional relation by providing a member that restricts relative movement of the power transmitting unit and the power receiving unit around the axis, or the like.

When the planar electrodes are disposed at the power transmitting unit and the power receiving unit, the same effect as the above-mentioned fourth embodiment can be obtained as long as the first covering member and the second covering member are formed of a conductive material instead of the magnetic body.

Further, in the power receiving unit 50A, like the above-mentioned power receiving unit 50, an example in which the member at which the planar electrode 58 is disposed is formed of a transparent resin has been described.

In addition, shapes of the power transmitting unit and the plate-shaped section are not limited to the above-mentioned substantial disc shape, and may be any of various shapes such as a polygonal shape or the like. Further, the power transmitting member and the power receiving member may not be disposed throughout the insertion section of the inserted medical device in the circumferential direction, and may be disposed at only a portion thereof in the circumferential direction like the power transmitting unit 72A of the modified example shown in FIG. 16.

However, in this case, when the power transmitting unit and the plate-shaped section are moved around the axis of the insertion section of the medical device relative to each other, since the planar coils or the like do not face each other and wireless power transmission may not be performed, a system is preferably configured to restrict relative movement of both of the power transmitting unit and the plate-shaped section around the axis with the restriction member or the like. As long as the relative movement of both of the power transmitting unit and the plate-shaped section is restricted, as the power transmitting unit and the plate-shaped section are integrally rotated about the axis of the insertion section, the power transmitting unit and the plate-shaped section can be moved to a position at which treatment is not interfered with.

Figure 16:
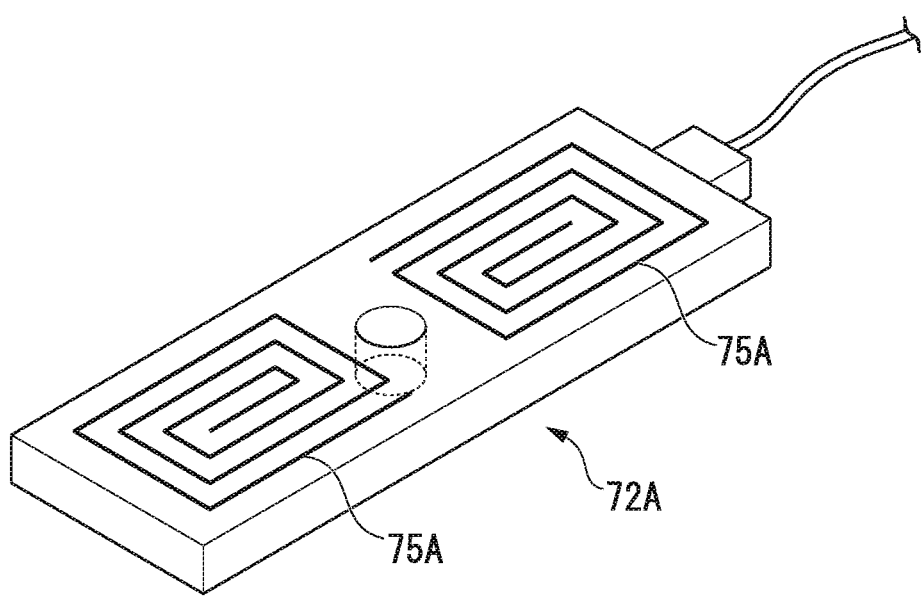
FIG. 16 is a perspective view showing another example of the power receiving unit of the medical power supply system of the present invention.

As shown in FIG. 16, a plurality of planar coils or planar electrodes may be provided at the power transmitting unit and the power receiving unit of the present invention. The planar coil may not be wound in a substantially circular shape, and may be wound in a polygonal shape like the planar coil 75A shown in FIG. 16.

An end effector of the present invention is not limited to the above-mentioned forceps, and may be any end effector as long as it is configured to receive power and exhibit a predetermined function. For example, the end effector may be a high-frequency knife used through electrical conduction or an observation means including an imaging element, an optical system, a lighting mechanism, and the like.

Further, the guide unit of the present invention is not limited to the above-mentioned trocar. Accordingly, the present invention can also be applied to an overtube or the like, which is used when an endoscope, a treatment tool, or the like is introduced into the body cavity, serving as the guide unit.

The present invention is not limited by the foregoing description, and is only limited by the appended claims.

What is claimed is:

1. A medical power supply system comprising:
  a medical device including an elongated insertion section, a distal end portion of which is provided with an end effector, a power receiving unit that includes a power receiving member and is movable relative to the insertion section in a longitudinal direction of the insertion section, and a biasing unit that biases the power receiving unit toward a distal end side of the insertion section; and
  a guide unit including a power transmitting unit at a proximal end side of the guide unit, the power transmitting unit including a power transmitting member connected to a power supply source, the insertion section of the medical device being inserted into the guide unit from the proximal end side of guide unit,
  wherein, when the insertion section is inserted into the guide unit to a predetermined amount,
  the power receiving unit comes in contact with the power transmitting unit in a state in which the power receiving unit is biased by the biasing unit, and
  the power transmitting member and the power receiving member face each other in an axial direction of the insertion section and have a positional relation in which wireless power transmission is possible.

2. The medical power supply system according to claim 1, wherein the power transmitting member and the power receiving member are planar coils, and wireless power transmission is performed through electromagnetic coupling of the power transmitting member and the power receiving member.

3. The medical power supply system according to claim 1, wherein the biasing unit is a biasing member that is elastically deformable.

4. The medical power supply system according to claim 1, wherein the biasing unit biases the power receiving unit using a magnetic force.

5. The medical power supply system according to claim 1, further comprising:
  a first cover formed of a magnetic body and disposed to cover a portion of an outer surface of the power receiving unit; and
  a second cover formed of a magnetic body and disposed to cover a portion of an outer surface of the power transmitting unit,
  wherein, when the power receiving unit comes in contact with the power transmitting unit, the first cover and the second cover surroundings of the power receiving member and the power transmitting member.

6. The medical power supply system according to claim 1, wherein the power transmitting member and the power receiving member are planar electrodes, and wireless power transmission is performed through electric field coupling of the power transmitting member and the power receiving member.

7. The medical power supply system according to claim 6, further comprising:
  a first cover formed of a conductive material and disposed to cover a portion of an outer surface of the power receiving unit; and
  a second cover formed of a conductive material and disposed to cover a portion of an outer surface of the power transmitting unit,
  wherein, when the power receiving unit comes in contact with the power transmitting unit, the first cover and the second cover surroundings of the power receiving member and the power transmitting member.

8. The medical power supply system according to claim 1, further comprising a restriction unit that is provided at at least one of the power receiving unit and the power transmitting unit and restricts relative movement between the power receiving unit and the power transmitting unit in a radial direction of the insertion section in a state in which the power receiving unit comes in contact with the power transmitting unit.

9. The medical power supply system according to claim 1, wherein the power receiving unit has a through-hole through which the insertion section is inserted.

* * * * *